United States Patent

Marumoto et al.

[11] 3,936,439
[45] Feb. 3, 1976

[54] 2,6-DIAMINONEBULARINE DERIVATIVES

[75] Inventors: Ryuji Marumoto; Yoshio Yoshioka; Mikio Honjo; Katsuyoshi Kawazoe, all of Osaka, Japan

[73] Assignee: Takeda Chemical Industries, Ltd., Osaka, Japan

[22] Filed: Nov. 30, 1973

[21] Appl. No.: 420,380

[30] Foreign Application Priority Data
Dec. 8, 1972  Japan............................. 47-123602
Oct. 11, 1973 Japan............................. 48-114542

[52] U.S. Cl.......................... 260/211.5 R; 424/180
[51] Int. Cl.².......................................... C07H 19/16
[58] Field of Search ............................. 260/211.5 R

[56]         References Cited
             UNITED STATES PATENTS

| 3,040,026 | 6/1962  | Duschinsky  | 260/211.5 R |
| 3,404,144 | 10/1968 | Fox et al.  | 260/211.5 R |
| 3,431,252 | 3/1969  | Walton      | 260/211.5 R |
| 3,590,029 | 6/1971  | Koch et al. | 260/211.5 R |
| 3,752,805 | 8/1973  | Maguire et al. | 260/211.5 R |

Primary Examiner—Johnnie R. Brown
Attorney, Agent, or Firm—Burgess Ryan and Wayne

[57]  ABSTRACT

Novel 2,6-diaminonebularine derivatives of the formula

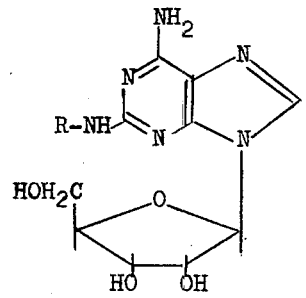

wherein R is a phenyl or cyclohexyl group which may be substituted with lower alkyl, lower alkoxy or halogen, and pharmaceutically acceptable salts thereof, exhibit excellent pharmacological acitivity such as strong and prolonged coronary dilating and platelet aggregation inhibitory actions.

15 Claims, No Drawings

2,6-DIAMINONEBULARINE DERIVATIVES

The present invention relates to novel and useful 2,6-diaminonebularine derivatives.

The present inventors have succeeded in producing novel 2,6-diaminonebularine derivatives of the formula

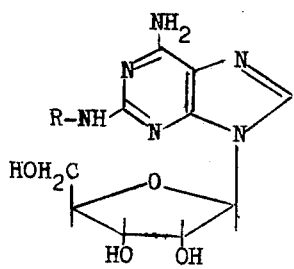

(I)

wherein R is a phenyl or cyclohexyl group which may be substituted with lower alkyl, lower alkoxy or halogen, and further studies on these compounds (I) have unexpectedly revealed that they exhibit excellent pharmacological activity such as strong and long-lasting coronary dilating and platelet aggregation inhibitory actions.

Thus, the principal object of the present invention is to provide the novel 2,6-diaminonebularine derivatives (I) which have the excellent pharmacological activity and another object is to provide a pharmaceutical composition comprising one or more of these compounds (I). A further object is to provide methods for the production of the novel and useful compounds (I).

Referring to the formula (I), R is a phenyl or cyclohexyl group which may be substituted with lower alkyl, lower alkoxy or halogen. The lower alkyl as the substituent may be of straight or branched chain, and may be advantageously those having up to four carbon atoms which are exemplified by methyl, ethyl, n-propyl, isopropyl, n-butyl and t-butyl. The lower alkoxy may be of straight or branched chain, and may be preferably those having up to four carbon atoms such as methoxy, ethoxy, isopropoxy and n-butoxy. The halogen may be any of chlorine, bromine, iodine and fluorine. The phenyl or cyclohexyl group may have one or more of these substituents at an optional position or positions of its ring.

The 2,6-diaminonebularine derivative of the formula (I) may be produced, for example, by reacting a 2-halogenoadenosine with an amine of the formula

R—NH$_2$ (II)

wherein R is as precedingly defined [Process I]; or alternatively by reacting a 6-substituted nebularine compound of the formula

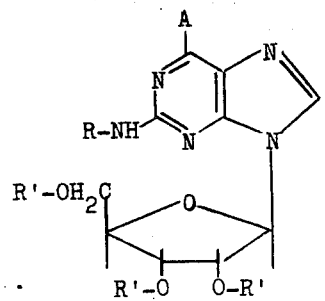

(III)

wherein R is as precedingly defined, A is an active radical which can react with ammonia to give an amino group and R' is hydrogen or an acyl group, with ammonia [Process II].

The 2-halogenoadenosine employed as the starting compound in Process I includes 2-fluoroadenosine, 2-chloroadenosine and 2-bromoadenosine. These compounds are per se known compounds and may be easily prepared, by, for example, the method described in "Journal of Heterocyclic Chemistry," 1, pp. 213–214.

In Process I, it is advantageous to employ about 1 to 10 moles of the amine (II) per mole of 2-halogenoadenosine. This reaction proceeds fast under heating at about 50° to 200°C and most expediently at about 110° to 150°C. If desired, one may employ an inert organic solvent such as methylcellosolve, dioxane or the like. It is also possible to add into the reaction system, by way of acid acceptor, such as a base as hydroxide of an alkali metal or alkaline earth metal (for example, sodium hydroxide, potassium hydroxide, lithium hydroxide, calcium hydroxide, barium hydroxide, etc.), the carbonate of the above metal (for example, sodium hydrogen carbonate, sodium carbonate, potassium carbonate, calcium carbonate, barium carbonate, etc.) or the salt of said metal with an organic acid (for example, sodium acetate, potassium acetate, etc.).

Referring to the compound (III) employed in Process II, the active radical A may be any group insofar as it is capable of reacting with ammonia to give an amino group. Thus, for example, halogens such as chlorine, bromine, fluorine, etc., and groups of the formula —SO$_n$R'' (R'' is hydrogen atom or alkyl or aralkyl group; and $n$ is 0, 1 or 2), such as mercapto, alkylmercapto, aralkylmercapto, alkylsulfine, alkylsulfone, etc., can be employed with advantage.

The acyl group for R' may be any of aliphatic, aromatic heterocyclic, saturated and unsaturated acyl groups such as acetyl, priopionyl, caproyl, palmitoyl, benzoyl, toluoyl, furoyl, and the like. A lower alkanoyl having up to four carbon atoms is most advantageous.

The 6-substituted nebularine compound (III) in which R' is an acyl group can be easily prepared, for example, by reacting a compound of the formula

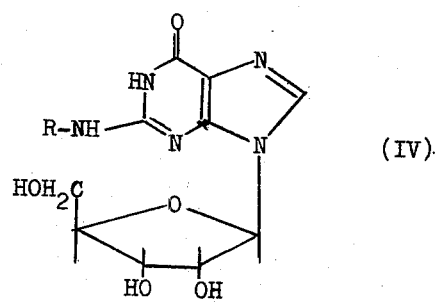

(IV)

wherein R is as precedingly defined with a reactive derivative of a carboxylic acid corresponding to the acyl group R', or reacting a compound of the formula

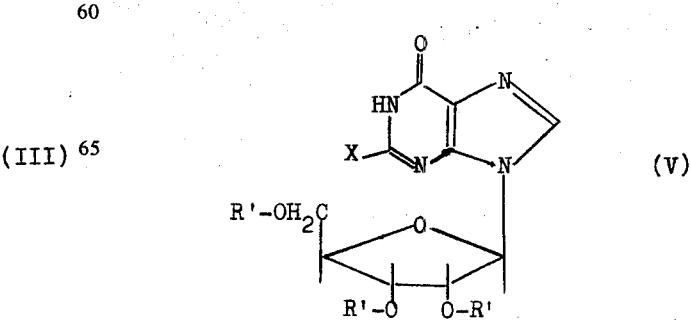

(V)

wherein R' is the acyl group and X is halogen with the amine of the formula (II) to yield a compound of the formula

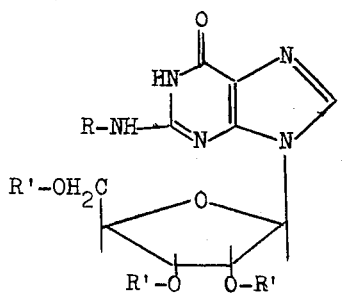

(VI)

wherein R is as precedingly defined and R' is the acyl group; and then, introducing the active radical into the 6-position of the thus-obtained compound (VI). The reaction of the compound (IV) with the reactive derivative of carboxylic acid such as carboxylic halide (e.g. chloride or bromide) and acid anhydride may be conducted in a per se known manner. It is advantageous to employ not less than 3 molecular equivalents, preferably about 5 to 15 molecular equivalents of such a reactive derivative as above for every mole of the compound (IV) in the presence of an organic solvent (e.g., benzene, chloroform, pyridine) at room temperature. The reaction of the compound (V) with the amine (II) may be performed after the manner mentioned above with regard to Process I, i.e., similarly to the reaction of the 2-halogenoadenosine with the amine (II). The specific means for introducing the active radical A into the compound (VI) to obtain the compound (III) can be selected according to the type of active radical A. When A is chlorine, for instance, the compound (VI) can be converted to the 6-chloro-compound by allowing, for example, phosphorus oxychloride to act upon the compound (VI) in the presence of an acid acceptor such as pyridine or alternatively causing thionyl chloride to act upon the same (VI) in the presence of dimethylformamide. In like fashion, the 6-mercapto-compound can be obtained by allowing phosphorus pentasulfide to act upon the compound (VI) in the presence of an acid acceptor and; by reacting the above compound further with an alkyl halide or aralkyl halide in the presence of an acid acceptor there can be obtained the corresponding 6-alkyl- or aralkyl-mercapto-compound. This 6-alkyl- or aralkyl-mercapto-compound, if reacted with hydrogen peroxide or N-chlorosuccinimide, gives rise to the 6-alkyl (aralkyl) sulfine or sulfone compound as the case may be.

A 6-substituted nebularine compound (III) in which R' is hydrogen can be easily prepared by subjecting the above-obtained compound (III) to per se known deacylation means, for example, the treatment with an alkali such as sodium hydroxide, sodium carbonate, sodium methylate or the like.

In reacting the 6-substituted nebularine compound of the formula (III) with ammonia in accordance with Process II of the present invention, it is, generally speaking, advantageous to dissolve ammonia in a solvent and employ not less than 1 molecular equivalent, preferably about 2 to 5 molecular equivalents, of ammonia for every molecular equivalent of the compound (III). The advantageous solvent is exemplified by lower alkanols (methanol, ethanol, etc.), methyl-cellosolve, water and mixtures of these solvents. Generally speaking, this reaction proceeds advantageously under heating at 100° to 200°C, and it is particularly advisable to heat the reaction mixture at that temperature in a gas-tight reactor. In this reaction the acyl group R' of the compound (III) splits off itself.

The 2,6-deaminonebularine derivatives thus-produced can be easily isolated from the reaction mixture by means which are known per se. A typical purification procedure may involve the steps of removing the excess amine (II) or ammonia and solvent, for instance, from the reaction mixture by distillation, washing the residue, for example, with chloroform and subjecting it to chromatography on a column of silica gel. In alternative purification scheme, the amine (II) or ammonia, solvent and so on are first distilled off from the reaction mixture and, then, an alcohol is added to the residue. The object 2,6-diaminonebularine derivative (I) can be converted into its pharmaceutically acceptable salts by conventional means. The typical examples of the pharmaceutically acceptable salts are mineral acid salts such as hydrochloride, sulfate and the like.

The novel 2,6-diaminonebularine derivatives (I) and the pharmaceutically acceptable salts thereof are characterized by their strong and long-lasting coronary dilating action as well as platelet aggregation inhibitory action, and are useful as coronary dilating and/or platelet aggregation inhibitory agents for mammals.

The following are the examples of the tests in which the coronary dilating action and platelet aggregation inhibitory action of illustrative compounds of the present invention are demonstrated in comparison with those of 2,6-diaminonebularine and $N^2$-ethyl-2,6-diaminonebularine which are known compounds.

Test for coronary dilating action

Each of dogs weighing 7 to 17 kilograms was anaesthetized with pentobarbital sodium salt (30 mg./kg., intravenously) and under supportive respiration, a left thoractomy was performed at the fifth interspace.

The heart of each animal was exposed and perfused with the blood guided from the animal's own left carotid artery to the left coronary artery circumflex through a polyethylene catheter. The coronary blood flow was measured with an electromagnetic flowmeter interposed in the external phase of the circuitry.

Each of the test compounds was administered directly into the coronary artery through the polyethylene catheter at a dose of 10 μg./dog. The potency of each compound was expressed with the potency of adenosine being taken as unity.

| Compound | Maximum coronary flow |
|---|---|
| Adenosine | 1.00 |
| $N^2$-Phenyl-2,6-diamino-nebularine | 6.75 |
| $N^2$-Cyclohexyl-2,6-diaminonebularine | 2.20 |
| $N^2$-(p-methoxyphenyl)-2,6-diaminonebularine | 2.37 |
| 2,6-Diaminonebularine | 0.50 |
| $N^2$-Ethyl-2,6-diaminonebularine | 0.91 |

Test for the action to inhibit the aggregation of rat platelets caused by adenosine-5'-diphosphate Using the platelet-rich plasmas of rats aged 8 to 10 weeks, the action was measured by the method of Born and Cross [J. Physiol, 168, 178 (1963)].

| Compound | Concentration ($\mu$g/ml) | Inhibitory action (%) | |
|---|---|---|---|
| | 370 | 74 | 15 |
| Adenosine | 0 | 0 | 0 |
| $N^2$-Phenyl-2,6-diaminonebularine | −85 | −52 | −38 |
| $N^2$-Cyclohexyl-2,6-diaminonebularine | −95 | −60 | −32 |
| 2,6-Diaminonebularine | 0 | 0 | 0 |
| $N^2$-Ethyl-2,6-diaminonebularine | −40 | −21 | −11 |

The 2,6-diaminonebularine derivatives (I) and their pharmaceutically acceptable salts may be administered alone or in combination with a pharmaceutically acceptable carrier or carriers. They are administrable in the forms of powders, tablets, solutions or emulsions for oral administration, or in the form of injectable liquid.

Pharmaceutical compositions containing one or more of the present compounds can be prepared by conventional methods for the preparation of powders, capsules, tablets, pills, injections and the like. The choice of carriers may be determined depending upon the route of administration, the solubility of the compounds (I) and so on.

The dose of the compounds (I) of the present invention may be chosen depending upon the route of administration, the species of mammals and purpose of administration. For instance, when the present compounds are orally administered to human adults for the purpose of treating coronary insufficiency or thrombosis, advantageous doses are in a range from 0.1 mg. to 20 mg. per day.

The following Examples are intended merely to illustrate presently preferred embodiments of the present invention and not to restrict the scope of this invention.

Throughout the foregoing description as well as in the following Examples and Claims, "$\mu$g.," "mg.," "kg.," "ml." "°C" and "N" respectively refer to "microgram(s)," "milligram(s)," "kilogram(s)," "milliliter(s)," "degrees centigrade" and "Normal(s)." In the Examples, the relationship between parts by weight and parts by volume corresponds to that between grams and milliliters.

EXAMPLE 1

To a solution of 12 parts by weight of 2-bromoadenosine in 200 parts by volume of methyl-cellosolve there is added 10 parts by volume of aniline. The mixture is heated at the bath temperature of 120°C for 16 hours. The reaction mixture is concentrated to dryness and ethyl ether is added to the residue to wash out the unreacted aniline. The ether-insoluble blackish brown material is dissolved in 10 parts by volume of methanol and, then, 10 parts by weight of silica gel is added.

After concentration to dryness, the material is placed on top of a column packed with 500 parts by weight of silica gel and chromatographic separation is carried out using a mixture of chloroform and methanol (9:1 by volume). Each fraction: 50 parts by volume. The 32nd to 50th fractions are pooled and concentrated to dryness. The resulting residue is recrystallized from first 2,000 parts by volume of ethanol and subsequently 1,500 parts by volume of hot water to obtain 4.9 parts by weight of $N^2$-phenyl-2,6-diaminonebularine in the form of colorless needles.

Melting point: 244°–245°C

Ultraviolet absorption spectrum:

$\lambda_{max}^{pH=5}$ : 244, 279 m$\mu$ $\lambda_{min}^{pH=5}$ : 257 m$\mu$

Elemental analysis: Calculated for $C_{16}H_{18}N_6O_4$(%): C, 53.62; H, 5.06; N, 23.45; Found: C, 53.43; H, 4.55; N, 23.95

3.6 Parts by weight of $N^2$-phenyl-2,6-diaminonebularine is dissolved in 500 parts by volume of 10% aqueous ethanol on heating at 100°C, followed by the addition of 10 parts by volume of 1N aqueous solution of hydrochloric acid. The solution is concentrated to 200 parts by volume and allowed to stand, whereby 3.1 parts by weight of $N^2$-phenyl-2,6-diaminonebularine hydrochloride is obtained in the form of needles.

Melting point: 184°–186°C

EXAMPLE 2

To a solution of 1 part by weight of 2-fluoroadenosine in 20 parts by volume of methyl-cellosolve there is added 0.8 part by volume of aniline and the mixture is heated at 120°C for 10 hours. The reaction mixture is then treated by a procedure similar to that described in Example 1 to obtain 0.43 part by weight of $N^2$-phenyl-2,6-diaminonebularine.

The melting point and ultraviolet absorption spectrum of this product are in complete agreement with those of the product of Example 1.

EXAMPLE 3

To a solution of 5 parts by weight of 2-chloroadenosine in 100 parts by volume of methyl-cellosolve there is added 5 parts by volume of cyclohexylamine, and the mixture is heated at the bath temperature of 150°C for 20 hours. The solvent is distilled off and the oily residue is dissolved in 200 parts by volume of ethanol and allowed to stand, whereupon crystals separate. These crude crystals are further recrystallized from 1,000 parts by volume of hot water. The procedure gives 4.2 parts by weight of $N^2$-cyclohexyl-2,6-diaminonebularine in the form of white needles.

Melting point: 148°–150°C

Ultraviolet absorption spectrum:

$\lambda_{max}^{pH=5}$ : 221, 259, 288 m$\mu$ $\lambda_{min}^{pH=5}$ : 242, 273 m$\mu$ Elemental analysis: Calculated for $C_{16}H_{24}N_6O_4 \cdot \frac{1}{2}H_2O$ (%): C, 51.46; H, 6.75; N, 22.51; Found: C, 51.42; H, 6.87; N, 22.02.

EXAMPLE 4 a. In 500 parts by volume of methanol is dissolved 60 parts by weight of 2-bromo-2',3',5'-tri-O-acetylinosine and, then, 75 parts by volume of aniline is added. The mixture is heated at 95°C for 3 hours. The reaction mixture is concentrated and allowed to stand, whereupon 35 parts by weight of crystals of 2-phenylamino-2',3',5'-tri-O-acetylinosine are obtained.
Melting point: 232°–233°C b. In 600 parts by volume of chloroform is suspended 23 parts by weight of 2-phenylamino-2',3',5'-tri-O-acetylinosine and under cooling with ice, 17 parts by volume of N,N-dimethylformamide and 53 parts by volume of thionyl chloride are added.

The mixture is boiled at the bath temperature of 90°C for 2 hours. Then, the solvent is distilled off and the residue is dissolved in 1,000 parts by volume of chloroform. The solution is combined with 1,000 parts by volume of ice-water and the mixture is neutralized with sodium hydrogen carbonate.

The chloroform layer is further washed twice with 500 parts by volume portions of water and, then, concentrated to dryness. The procedure gives 24 parts by weight of a yellowish brown resinous product. This is then purified by column chromatography on 500 parts by weight of silica gel with use of 5,000 parts by volume of a mixture of chloroform and methanol (99:1 by volume) to obtain 18 parts by weight of 6-chloro-2-phenylamino-2',3',5'-tri-O-acetylnebularine as a pale yellowish resinous product. Nuclear magnetic resonance spectrum ($d_6$-dimethylsulfoxide) $\delta$ : 3.10; 3.03(9H, 3COCH$_3$), 4.3(3H, m, H$_4'$ , 2H$_5'$ ), 4.90(1H, m, H$_3'$ ), 6.0(2H, m, H$_1'$ and H$_2'$ ), 7.0–8.0(5H, m, phenyl), 8.05(LH, s, H$_8$), 10.0(1H, s,

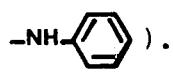).

c. In 300 parts by volume of 20% methanolic ammonia is dissolved 17.5 parts by weight of 6-chloro-2-phenylamino-2', 3',5'-tri-O-acetylnebularine and the solution is heated in a sealed tube at 120°C for 4 hours. The reaction mixture is concentrated and the crystals separating out are harvested by filtration. Recrystallization from 3,000 parts by volume of hot water gives 9.5 parts by weight of N$^2$-phenyl-2,6-diaminonebularine in the form of colorless needles.
Melting point: 244°–245°C
Ultraviolet absorption spectrum $\lambda_{max}^{pH=2}$ m$\mu(\epsilon)$: 230(shoulder), 272(16800); $\lambda_{max}^{pH=12}$ m$\mu(\epsilon)$: 242(16500), 277(19700)

Elemental analysis: Calculated for C$_{16}$H$_{18}$N$_6$O$_4$ (%): C, 53.62; H, 5.06; N, 23.45; Found: C, 53.33; H, 5.10; N, 22.75.

EXAMPLE 5

In 100 parts by volume of pyridine is suspended 10 parts by weight of 2-phenylaminoinosine and 50 parts by weight of acetic anhydride is added dropwise. The mixture is stirred for 3 hours, at the end of which time it is concentrated under reduced pressure. The residue is recrystallized from 5 parts by volume of methanol. The procedure gives 2 parts by weight of 2-phenylamino-2',3',5'-tri-O-acetylinosine in the form of colorless flocs.
Melting point: 234°–235°C In a manner similar to the procedure of Example 4 (b), the above-obtained 2-phenylamino-2',3',5'-tri-O-acetylinosine is 6-chlorinated and, then, by a procedure similar to that described in Example 4 (c) above, treated with ammonia. The procedures give 0.89 part by weight of N$^2$-phenyl-2,6-diaminonebularine.
Melting point: 244°–245°C.

EXAMPLE 6

In 500 parts by volume of pyridine is dissolved 20 parts by weight of 2-phenylamino-2',3',5'-tri-O-acetylinosine, followed by the addition of 60 parts by weight of phosphorus pentasulfide. The mixture is boiled for 5 hours, after which time it is poured in 2,000 parts by volume of ice-water. After stirring for 1 hour, the precipitate is harvested by filtration. This is dissolved in 300 parts by volume of chloroform and, after the insolubles are filtered off, the solution is concentrated to dryness. The residue is dissolved in 300 parts by volume of 50 % aqueous methanol, followed by the addition of 150 parts by volume of 2N sodium hydroxide and 25 parts by volume of methyl iodide. The mixture is stirred at room temperature for 20 hours. The reaction mixture is concentrated to dryness and the residue is dissolved again in 500 parts by volume of 50 % aqueous methanol. The solution is adjusted to pH 3 and, then, diluted up to 2,000 parts by volume with water. The dilution is then run onto a column of activated carbon (200 parts by weight). The column is washed with water and, then, eluted with 2,000 parts by volume of a mixed eluant of water-ethanol-butanol-28 % aqueous ammonia (48:45:5:2 by volume). The eluate is concentrated to dryness and the residue, N$^2$-phenyl-6-methylmercapto-2-aminonebularine, is dissolved in 150 parts by volume of 20 % methanolic ammonia. Then, the reaction procedure of Example 4(c) is followed to obtain 10.5 parts by weight of N$^2$-phenyl-2,6-diaminonebularine.
Melting point: 244°–245°C

EXAMPLE 7

By a procedure similar to that of Example 4(a), 1 part by weight of 2-cyclohexylaminoinosine is reacted with 5 parts by volume of acetic anhydride to obtain 1.1 parts by weight of 2-cyclohexylamino-2',3',5'-tri-O-acetylinosine as a colorless resinous product.
Ultraviolet absorption spectrum: $\lambda_{max}^{MeOH}$ 257, 285(shoulder) m$\mu$.

In a manner similar to Example 4(b), 0.5 part by weight of this product is reacted with thionyl chloride in the presence of dimethylformamide, whereupon 0.44 part by weight of 6-chloro-2-cyclohexylamino-2',3',5'-tri-O-acetylnebularine is obtained in the form of a colorless resin. This is dissolved in 20 parts by volume of 20% methanolic ammonia and reacted in the same manner as Example 4(c). The procedure gives 0.23 part by weight of N$^2$-cyclohexyl-2,6-diaminonebularine.
Melting point: 148°–150°C

EXAMPLE 8

The reaction between 2-halogenoadenosine with the amine (II) [Process I] and the reaction of the compound (III) with ammonia [Process II] are respectively conducted in the same procedures as in the preceding Examples to obtain the compounds listed in Table 1, which are novel and useful and fall within the scope of the formula (I).

Table 1

| Compound | Molecular formula | Elemental analysis Calculated (%) | | Found (%) | | Melting point and ultraviolet absorption spectrum | |
|---|---|---|---|---|---|---|---|
| $N^2$-(p-methoxyphenyl)-2,6-diaminonebularine | $C_{17}H_{20}N_6O_5$ | C | 52.57 | C | 52.33 | Melting point: 195°–197°C | |
| | | H | 5.19 | H | 4.76 | | |
| | | N | 21.64 | N | 21.73 | | |
| $N^2$-(p-methylphenyl)-2,6-diaminonebularine | $C_{17}H_{20}N_6O_4$ | C | 54.83 | C | 54.67 | Melting point: 164°–165°C | |
| | | H | 5.41 | H | 5.12 | | |
| | | N | 22.57 | N | 22.91 | | |
| $N^2$-(p-chlorophenyl)-2,6-diaminonebularine | $C_{16}H_{17}N_6O_4Cl$ | C | 48.92 | C | 49.34 | MeOH: $\gamma$max | 252,268(shoulder), 274,290(shoulder) |
| | | H | 4.36 | H | 4.13 | | m$\mu$ |
| | | N | 21.39 | N | 20.97 | MeOH: $\gamma$min | 230,259 m$\mu$ |
| $N^2$-(p-methylcyclohexyl)-2,6-diaminonebularine | $C_{17}H_{26}N_6O_4$ | C | 53.95 | C | 53.72 | pH=5: $\gamma$max | 222,259,288 m$\mu$ |
| | | H | 6.93 | H | 6.98 | | |
| | | N | 22.21 | N | 21.86 | pH=5: $\gamma$min | 242,273 m$\mu$ |

EXAMPLE 9

Some examples of formulation in which the compounds of this invention are utilized as coronary dilating and/or platelet aggregation inhibitory agents are as follows:

A. (Tablet)
| | |
|---|---|
| (1) $N^2$-phenyl-2,6-diaminonebularine | 20 mg. |
| (2) lactose | 35 mg. |
| (3) corn starch | 150 mg. |
| (4) microcrystalline cellulose | 30 mg. |
| (5) magnesium stearate | 5 mg. |
| | 240 mg. per tablet |

(1),(2),(3), two-thirds quantity of (4) and half of the quantity of (5) are thoroughly mixed, and then the mixture is granulated. The remaining one-third quantity of (4) and half of (5) are added to the granules and compressed into tablets. The thus prepared tablets can further be coated with a suitable coating agent, e.g., sugar.

B. (Capsule)
| | |
|---|---|
| (1) $N^2$-cyclohexyl-2,6-diaminonebularine | 20 mg. |
| (2) lactose | 102 mg. |
| (3) microcrystalline cellulose | 70 mg. |
| (4) magnesium stearate | 8 mg. |
| | 200 mg. per capsule |

(1),(2),(3) and half of the quantity of (4) are thoroughly mixed, and then the mixture is granulated. The remaining half of (4) is added to the granules and the whole is filled into a gelatin capsule.

C. (Injectable)
| | |
|---|---|
| (1) $N^2$-phenyl-2,6-diaminonebularine hydrochloride | 10 mg. |
| (2) inositol | 100 mg. |
| (3) benzyl alcohol | 20 mg. |

All ingredients are dissolved in water to make 2.0 ml. of the solution (pH 7.5) serving as an injectable.

What is claimed is:

1. A 2,6-diaminonebularine derivative of the formula

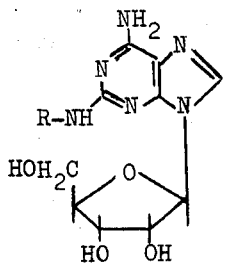

wherein R is a phenyl or cyclohexyl group which may be substituted with lower alkyl, lower alkoxy or halogen, or pharmaceutically acceptable mineral acid salts thereof.

2. The 2,6-diaminonebularine derivative according to claim 1, wherein the mineral acid salt is a hydrochloride.

3. The 2,6-diaminonebularine derivative according to claim 1, wherein R is a phenyl group which may be substituted with lower alkyl, lower alkoxy or halogen.

4. The 2,6-diaminonebularine derivative according to claim 3, wherein R is a phenyl group substituted with a lower alkyl having up to four carbon atoms.

5. The 2,6-diaminonebularine derivative according to claim 3, wherein R is a phenyl group substituted with a lower alkoxy having up to four carbon atoms.

6. The 2,6-diaminonebularine derivative according to claim 3, wherein R is a phenyl group substituted with halogen.

7. The 2,6-diaminonebularine derivative according to claim 1, wherein R is a cyclohexyl group which may be substituted with lower alkyl, lower alkoxy or halogen.

8. The 2,6-diaminonebularine derivative according to claim 7, wherein R is a cyclohexyl group substituted with a lower alkyl having up to four carbon atoms.

9. The 2,6-diaminonebularine derivative according to claim 1, which is $N^2$-phenyl-2,6-diaminonebularine.

10. The 2,6-diaminonebularine derivative according to claim 1, which is $N^2$-(p-methylphenyl)-2,6-diaminonebularine.

11. The 2,6-diaminonebularine derivative according to claim 1, which is $N^2$-(p-methoxyphenyl)2,6-diaminonebularine.

12. The 2,6-diaminonebularine derivative according to claim 1, which is $N^2$-(p-chlorophenyl)-2,6-diaminonebularine.

13. The 2,6-diaminonebularine derivative according to claim 1, which is $N^2$-cyclohexyl-2,6-diaminonebularine.

14. The 2,6-diaminonebularine derivative according to claim 1, which is $N^2$-(p-methylcyclohexyl)-2,6-diaminonebularine.

15. A 2,6-diaminonebularine derivative according to claim 1 which is $N^2$-phenyl-2,6-diaminonebularine hydrochloride.

* * * * *